(12) United States Patent
Han et al.

(10) Patent No.: US 11,618,759 B2
(45) Date of Patent: Apr. 4, 2023

(54) LIGAND COMPOUND, TRANSITION METAL COMPOUND, AND CATALYST COMPOSITION INCLUDING THE SAME

(71) Applicant: LG Chem, Ltd., Seoul (KR)

(72) Inventors: Ki Won Han, Daejeon (KR); A Rim Kim, Daejeon (KR); Seung Hwan Jung, Daejeon (KR)

(73) Assignee: LG Chem, Ltd.

( * ) Notice: Subject to any disclaimer, the term of this patent is extended or adjusted under 35 U.S.C. 154(b) by 0 days.

(21) Appl. No.: 17/582,561

(22) Filed: Jan. 24, 2022

(65) Prior Publication Data

US 2022/0144773 A1 May 12, 2022

Related U.S. Application Data

(62) Division of application No. 16/643,205, filed as application No. PCT/KR2019/000474 on Jan. 11, 2019, now Pat. No. 11,274,113.

(30) Foreign Application Priority Data

Jan. 12, 2018 (KR) ........................ 10-2018-0004397

(51) Int. Cl.
| | |
|---|---|
| C07D 209/86 | (2006.01) |
| C07D 409/04 | (2006.01) |
| C07D 417/04 | (2006.01) |
| C07D 413/04 | (2006.01) |
| C07D 265/38 | (2006.01) |
| C07F 17/00 | (2006.01) |
| C07F 7/28 | (2006.01) |
| C08F 4/642 | (2006.01) |
| C08F 4/659 | (2006.01) |
| C08F 4/6592 | (2006.01) |
| C08F 210/16 | (2006.01) |
| B01J 31/18 | (2006.01) |

(52) U.S. Cl.
CPC ............ *C07F 7/28* (2013.01); *B01J 31/1825* (2013.01); *C07D 209/86* (2013.01); *C07D 265/38* (2013.01); *C07D 409/04* (2013.01); *C07D 413/04* (2013.01); *C07D 417/04* (2013.01); *C07F 17/00* (2013.01); *C08F 4/642* (2013.01); *C08F 4/6592* (2013.01); *C08F 4/65916* (2013.01); *C08F 210/16* (2013.01); *B01J 2531/46* (2013.01)

(58) Field of Classification Search
CPC .. C07D 209/86; C07D 409/04; C07D 417/04; C07D 413/04; C07D 265/38; C07F 17/00
See application file for complete search history.

(56) References Cited

U.S. PATENT DOCUMENTS

| | | |
|---|---|---|
| 5,064,802 A | 11/1991 | Stevens et al. |
| 6,548,686 B2 | 4/2003 | Nabika et al. |
| 2007/0225158 A1 | 9/2007 | Lee et al. |
| 2010/0062927 A1 | 3/2010 | Lee et al. |
| 2010/0093959 A1 | 4/2010 | Hong et al. |
| 2015/0239916 A1 | 8/2015 | Do et al. |
| 2016/0046735 A1 | 2/2016 | Lee et al. |
| 2016/0122455 A1 | 5/2016 | Berthoud et al. |
| 2017/0349674 A1 | 12/2017 | Cho et al. |
| 2017/0355786 A1 | 12/2017 | Duchateau et al. |
| 2018/0002461 A1 | 1/2018 | Joung et al. |

FOREIGN PATENT DOCUMENTS

| | | |
|---|---|---|
| CN | 101213218 A | 7/2008 |
| CN | 102936301 B | 4/2015 |
| CN | 104703994 A | 6/2015 |
| CN | 104797586 A | 7/2015 |
| CN | 105209472 A | 12/2015 |
| CN | 107108674 A | 8/2017 |
| CN | 107207660 A | 9/2017 |
| EP | 3037438 A1 | 6/2016 |
| JP | 2003155291 A | 5/2003 |
| JP | 2015193612 A | 11/2015 |
| KR | 101237467 B1 | 2/2013 |
| KR | 20150044413 A | 4/2015 |
| KR | 20150121595 A | 10/2015 |
| KR | 20160005034 A | 1/2016 |
| KR | 20160077488 A | 7/2016 |
| KR | 20170004397 A | 1/2017 |
| KR | 20170074675 A | 6/2017 |

OTHER PUBLICATIONS

Chen et al., "A Novel Phenolate "Constrained Geometry" Catalyst System. Efficient Synthesis, Structural Characterization, and r-Olefin Polymerization Catalysis", Organometallics, vol. 16, No. 26, Dec. 1997, pp. 5958-5963.
Christie et al., "Novel Routes to Bidentate Cyclopentadienyl-Alkoxide Complexes of Titanium: Synthesis of (n5-ó-C5R14CHR2CH2CR3R4O)TiC12", Organometallics, vol. 18, No. 3, Jan. 1999, pp. 348-359.
Gibson et al., "Advances in Non-Metallocene Olefin Polymerization Catalysis", Chemical Reviews, vol. 103, No. 1, Dec. 2002, pp. 283-315.
Gielens et al., "Titanium Hydrocarbyl Complexes with a Linked Cyclopentadienyl-Alkoxide Ancillary Ligand; Participation of the Ligand in an Unusual Activation of a (Trimethylsilyl)methyl Group", Organometallics, vol. 17, No. 9, Apr. 1998, pp. 1652-1654.
International Search Report from Application No. PCT/KR2019/000474 dated Apr. 15, 2019, 2 pages.
Rau et al., "Synthesis and application in high-pressure polymerization of a titanium complex with a linked cyclopentadienyl-phenoxide ligand", Journal of Organometallic Chemistry, vol. 608, Feb. 2000, pp. 71-75.
Turner et al., "Facile resolution of constrained geometry indenyl-phenoxide ligation", Chemical Communications, Mar. 2003, pp. 1034-1035.

(Continued)

*Primary Examiner* — Caixia Lu
(74) *Attorney, Agent, or Firm* — Lerner, David, Littenberg, Krumholz & Mentlik, LLP

(57) ABSTRACT

The present invention provides a novel ligand compound, a transition metal compound and a catalyst composition including the same.

2 Claims, No Drawings

(56) References Cited

OTHER PUBLICATIONS

Zhang et al., "Constrained Geometry Tetramethylcyclopentadienyl-phenoxytitanium Dichlorides: Template Synthesis, Structures, and Catalytic Properties for Ethylene Polymerization", Organometallics, vol. 23, No. 3, Dec. 2003, pp. 540-546.
Search Report dated May 16, 2022 from the Office Action for Chinese Application No. 201980004169.5 dated May 20, 2022, pp. 1-3. [See p. 1, categorizing the cited references].

LIGAND COMPOUND, TRANSITION METAL COMPOUND, AND CATALYST COMPOSITION INCLUDING THE SAME

CROSS-REFERENCE TO RELATED APPLICATIONS

The present application is a divisional application of U.S. application Ser. No. 16/643,205 filed Feb. 28, 2020, a national phase entry under 35 U.S.C. § 371 of International Application No. PCT/KR2019/000474 filed Jan. 11, 2019, which claims priority from Korean Patent Application No. 2018-0004397 filed Jan. 12, 2018, all of which are incorporated herein by reference.

TECHNICAL FIELD

The present invention relates to a ligand compound, a transition metal compound, and a catalyst composition including the same.

BACKGROUND ART

[Me$_2$Si(Me$_4$C$_5$)NtBu]TiCl$_2$ (Constrained-Geometry Catalyst, hereinafter, will be abbreviated as CGC) was reported by Dow Co. in the early 1990s (U.S. Pat. No. 5,064,802), and excellent aspects of the CGC in the copolymerization reaction of ethylene and alpha-olefin may be summarized in the following two points when compared to commonly known metallocene catalysts: (1) at a high polymerization temperature, high activity is shown and a polymer having high molecular weight is produced, and (2) the copolymerization degree of alpha-olefin having large steric hindrance such as 1-hexene and 1-octene is excellent. In addition, as various properties of the CGC during performing a polymerization reaction are gradually known, efforts of synthesizing the derivatives thereof and using as a polymerization catalyst has been actively conducted in academy and industry.

As one approach, the synthesis of a metal compound introducing various bridges instead of a silicon bridge and a nitrogen substituent and the polymerization thereof has been conducted. Typical metal compounds known until now are illustrated as Compounds (1) to (4) below (Chem. Rev. 2003, 103, 283).

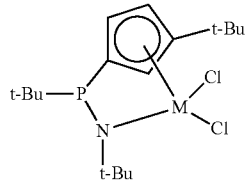

(1)

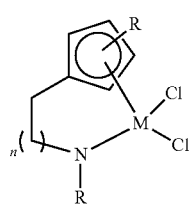

(2)

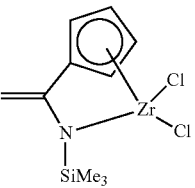

(3)

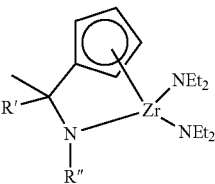

(4)

The above Compounds (1) to (4) introduce a phosphorous bridge (1), an ethylene or propylene bridge (2), a methylidene bridge (3) or a methylene bridge (4) instead of the silicon bridge of a CGC structure. However, improved results on activity, copolymerization performance, etc. could not be obtained by applying an ethylene polymerization or a copolymerization with alpha-olefin when compared to those obtained by applying the CGC.

In addition, as another approach, a lot of compounds composed of an oxido ligand instead of the amido ligand of the CGC have been synthesized, and an attempt on the polymerization using thereof has been conducted to some extent. Examples thereof are summarized in the following.

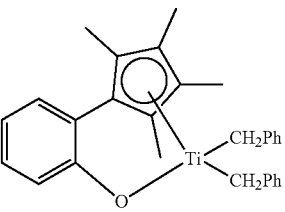

(5)

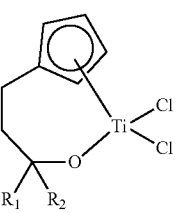

(6)

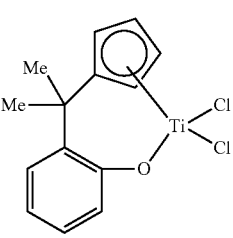

(7)

-continued (8)

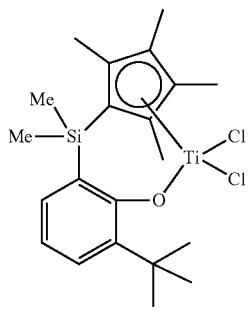

Compound (5) has been reported by T. J. Marks et al. and is characterized in that a cyclopentadiene (Cp) derivative and an oxido ligand are bridged via an ortho-phenylene group (Organometallics 1997, 16, 5958). A compound having the same bridged group and a polymerization using thereof have been reported by Mu et al. (Organometallics 2004, 23, 540). In addition, the bridging of an indenyl ligand and an oxido ligand by the same ortho-phenylene group has been reported by Rothwell et al. (Chem. Commun. 2003, 1034). Compound (6) has been reported by Whitby et al. and is characterized in that a cyclopentadienyl ligand and an oxido ligand are bridged by three carbon atoms (Organometallics 1999, 18, 348). The above catalysts have been reported to show activity in a syndiotactic polystyrene polymerization. Similar compounds have been also reported by Hessen et al. (Organometallics 1998, 17, 1652). Compound (7) has been reported by Rau et al. and is characterized in showing activity in an ethylene polymerization and an ethylene/1-hexene copolymerization at a high temperature and high pressure (210° C., 150 MPa) (J. Organomet. Chem. 2000, 608, 71). In addition, the synthesis of a catalyst (8) having similar structure as that of Compound (7) and a polymerization using the same at a high temperature and a high pressure have been filed by Sumitomo Co. (U.S. Pat. No. 6,548,686). However, not many catalysts among the above attempts are practically applied in commercial plants.

Accordingly, a catalyst which is capable of preparing polyolefin elastomer having a high molecular weight in a low density region and shows excellent polymerization performance is required, and a simple preparation method of the catalyst is required.

PRIOR ART DOCUMENTS

Patent Documents (Patent Document 1) U.S. Pat. No. 5,064,802
(Patent Document 2) U.S. Pat. No. 6,548,686

Non-Patent Documents (Non-patent Document 1) Chem. Rev. 2003, 103, 283
(Non-patent Document 2) Organometallics 1997, 16, 5958
(Non-patent Document 3) Organometallics 2004, 23, 540
(Non-patent Document 4) Chem. Commun. 2003, 1034
(Non-patent Document 5) Organometallics 1999, 18, 348
(Non-patent Document 6) Organometallics 1998, 17, 1652
(Non-patent Document 7) J. Organomet. Chem. 2000, 608, 71

DISCLOSURE OF THE INVENTION

Technical Problem

An object of the present invention is to provide a novel ligand compound, a transition metal compound using the same and a catalyst composition including the same.

In addition, another object of the present invention is to provide a method for preparing a polymer having a low density and high molecular weight by using the catalyst composition.

Technical Solution

An embodiment of the present invention provides a transition metal compound represented by the following Formula 1:

[Formula 1]

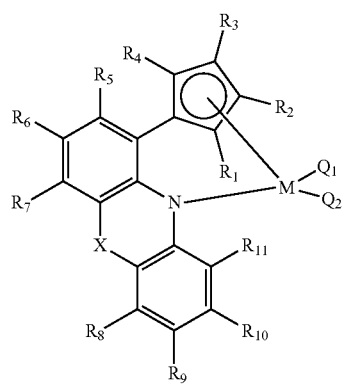

X is O, S or a single bond;

M is a transition metal in group 4;

$Q_1$ and $Q_2$ are each independently hydrogen; a halogen group; an alkyl group of 1 to 20 carbon atoms; a cycloalkyl group of 3 to 20 carbon atoms; an alkenyl group of 2 to 20 carbon atoms; an aryl group of 6 to 20 carbon atoms; an alkylaryl group of 7 to 20 carbon atoms; an arylalkyl group of 7 to 20 carbon atoms; an alkylamino group of 1 to 20 carbon atoms; or an arylamino group of 6 to 20 carbon atoms, $R_1$ to $R_4$ are each independently hydrogen; a silyl group; an alkyl group of 1 to 20 carbon atoms; an alkenyl group of 2 to 20 carbon atoms; a cycloalkyl group of 3 to 20 carbon atoms; an aryl group of 6 to 20 carbon atoms; an alkylaryl group of 7 to 20 carbon atoms; an arylalkyl group of 7 to 20 carbon atoms; or a metalloid radical of a metal in group 14, which is substituted with a hydrocarbyl group of 1 to 20 carbon atoms, where adjacent two or more among $R_1$ to $R_4$ may be connected with each other to form an aliphatic ring of 3 to 20 carbon atoms, an aromatic ring of 6 to 20 carbon atoms or a heteroaromatic ring of 4 to 20 carbon atoms; and $R_5$ to $R_{11}$ are each independently hydrogen; a silyl group; a halogen group; an alkyl group of 1 to 20 carbon atoms; an alkenyl group of 2 to 20 carbon atoms; a cycloalkyl group of 3 to 20 carbon atoms; an aryl group of 6 to 20 carbon atoms; an arylalkyl group of 7 to 20 carbon atoms; an alkylaryl group of 7 to 20 carbon atoms; an alkoxy group of 1 to 20 carbon atoms; or an aryloxy group of 6 to 20 carbon atoms; where adjacent two or more among $R_5$ to $R_{11}$ may be connected with each other to form an aliphatic ring of 3 to 20 carbon atoms, or an aromatic ring of 6 to 20 carbon atoms.

Another embodiment of the present invention provides a ligand compound represented by the following Formula 2:

[Formula 2]

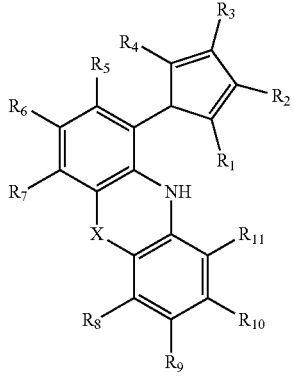

X is O, S or a single bond;
$R_1$ to $R_4$ are each independently hydrogen; a silyl group; an alkyl group of 1 to 20 carbon atoms; an alkenyl group of 2 to 20 carbon atoms; a cycloalkyl group of 3 to 20 carbon atoms; an aryl group of 6 to 20 carbon atoms; an alkylaryl group of 7 to 20 carbon atoms; an arylalkyl group of 7 to 20 carbon atoms; or a metalloid radical of a metal in group 14, which is substituted with a hydrocarbyl group of 1 to 20 carbon atoms, where adjacent two or more among $R_1$ to $R_4$ may be connected with each other to form an aliphatic ring of 3 to 20 carbon atoms, an aromatic ring of 6 to 20 carbon atoms or a heteroaromatic ring of 4 to 20 carbon atoms; and $R_5$ to $R_{11}$ are each independently hydrogen; a silyl group; a halogen group; an alkyl group of 1 to 20 carbon atoms; an alkenyl group of 2 to 20 carbon atoms; a cycloalkyl group of 3 to 20 carbon atoms; an aryl group of 6 to 20 carbon atoms; an arylalkyl group of 7 to 20 carbon atoms; an alkylaryl group of 7 to 20 carbon atoms; an alkoxy group of 1 to 20 carbon atoms; or an aryloxy group of 6 to 20 carbon atoms; where adjacent two or more among $R_5$ to $R_{11}$ may be connected with each other to form an aliphatic ring of 3 to 20 carbon atoms, or an aromatic ring of 6 to 20 carbon atoms.

Another embodiment of the present invention provides a method for preparing the transition metal compound of Formula 1 by reacting a compound represented by the following Formula 2 with a compound represented by the following Formula 3 and an organolithium compound:

[Formula 2]

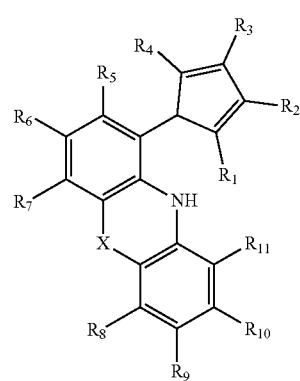

$M(Q_1Q_2)_2$ [Formula 3]

In the above formulae, M, X, $Q_1$, $Q_2$ and $R_1$ to $R_{11}$ are the same as defined above.

Another embodiment of the present invention provides a catalyst composition for polymerizing polyolefin, including the transition metal compound.

Another embodiment of the present invention provides a method for preparing a polymer using the catalyst composition.

Advantageous Effects

The catalyst composition including the novel ligand compound and the transition metal compound of the present invention may be useful as a catalyst in a polymerization reaction for preparing an olefin-based polymer. Particularly, if the catalyst composition including the novel ligand compound and the transition metal compound of the present invention is applied for polymerizing olefin, the copolymerization properties of higher alpha olefin (HAO) is excellent, and polyolefin elastomer with a low density may be prepared.

In addition, polyolefin elastomer having a high molecular weight and a low melting index (MI) may be prepared by using the catalyst composition including the novel ligand compound and the transition metal compound of the present invention.

BEST MODE FOR CARRYING OUT THE INVENTION

Hereinafter, the present invention will be described in more detail in order to assist the understanding of the present invention.

It will be understood that words or terms used in the description and claims of the present invention shall not be interpreted as the meaning defined in commonly used dictionaries. It will be further understood that the words or terms should be interpreted as having a meaning that is consistent with their meaning of the technical idea of the invention, based on the principle that an inventor may properly define the meaning of the words or terms to best explain the invention.

It will be understood that the terms "comprises", "includes" or "has" when used in this specification, specify the presence of stated features, numerals, steps, elements or the combination thereof, but do not preclude the presence or addition of one or more other features, numerals, steps, elements or the combination thereof.

In the whole disclosure, "catalyst composition" or "catalyst system" means a state obtainable as a catalyst composition having activity by adding three components including a transition metal source, a ligand compound and a cocatalyst or alternatively, two components of a transition metal compound and a cocatalyst, at the same time or in an optional order. The three components or two components of the catalyst composition may be added in the presence or absence of a solvent and a monomer.

In the present disclosure, the term "halogen" means fluorine, chlorine, bromine or iodine, unless otherwise noted.

In the present disclosure, "silyl" may be silyl which is substituted with an alkyl group of 1 to 20 carbon atoms, for example, trimethylsilyl or triethylsilyl.

In the present disclosure, "hydrocarbyl group" means all compounds composed of only carbon and hydrogen, for example, an alkyl group, an aryl group, an alkenyl group, a cycloalkyl group, etc. The term of the hydrocarbyl group may mean both linear or branch type and both unsubstituted and substituted type, unless otherwise noted. For example, an alkyl group of 1 to 20 carbon atoms may mean a methyl group, an ethyl group, a propyl group, an isopropyl group, a butyl group, an isobutyl group, a pentyl group, an isopentyl group, a neopentyl group, etc., and an aryl group of 6 to 20 carbon atoms may mean, for example, a phenyl group, a naphthyl group, an anthracenyl group, etc., without limitation.

In the present disclosure, the term "alkyl" means linear, cyclic or branched hydrocarbon residue unless otherwise noted.

In the present disclosure, the term "cycloalkyl" means a cyclic alkyl group including cyclopropyl unless otherwise noted.

In the present disclosure, the term "alkenyl" means a linear or branched alkenyl group unless otherwise noted.

In the present disclosure, the term "aryl" means an aromatic group such as phenyl, naphthyl, anthryl, phenanthryl, chrysenyl, and pyrenyl unless otherwise noted.

In the present disclosure, "alkylaryl group" means an aryl group having one or more alkyl groups as substituents, and "arylalkyl group" means an alkyl group having one or more aryl groups as substituents.

In the present disclosure, "heteroatom" means N, O, S, P, and "heteroalkyl group" means an alkyl group including one or more heteroatoms. That is, the heteroalkyl group may mean an alkyl group in which any one among constituent carbon is substituted with a heteroatom, or a heteroatom is included as a substituent. "Heteroaryl group" may mean an aryl group in which any one among carbon of an aromatic ring is substituted with a heteroatom like a pyridyl group. "Heteroaromatic ring" may mean an aromatic ring containing a heteroatom. Besides, a heteroarylalkyl group, a heteroalkylaryl group, a heteroalkenylaryl group, etc. may be the same.

The catalyst composition shows high activity in a high polymerization temperature and if applied for the polymerization of olefin using the same, polyolefin elastomer having excellent alpha olefin selectivity and a high molecular weight may be produced.

An embodiment of the present invention provides a transition metal compound represented by the following Formula 1:

[Formula 1]

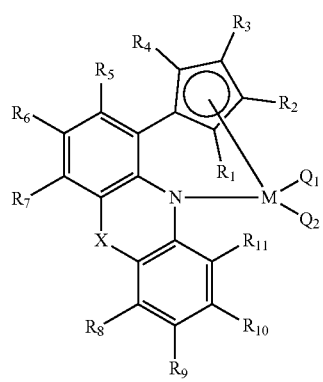

X is O, S or a single bond;
M is a transition metal in group 4;

$Q_1$ and $Q_2$ are each independently hydrogen; a halogen group; an alkyl group of 1 to 20 carbon atoms; a cycloalkyl group of 3 to 20 carbon atoms; an alkenyl group of 2 to 20 carbon atoms; an aryl group of 6 to 20 carbon atoms; an alkylaryl group of 7 to 20 carbon atoms; an arylalkyl group of 7 to 20 carbon atoms; an alkylamino group of 1 to 20 carbon atoms; or an arylamino group of 6 to 20 carbon atoms, $R_1$ to $R_4$ are each independently hydrogen; a silyl group; an alkyl group of 1 to 20 carbon atoms; an alkenyl group of 2 to 20 carbon atoms; a cycloalkyl group of 3 to 20 carbon atoms; an aryl group of 6 to 20 carbon atoms; an alkylaryl group of 7 to 20 carbon atoms; an arylalkyl group of 7 to 20 carbon atoms; or a metalloid radical of a metal in group 14, which is substituted with a hydrocarbyl group of 1 to 20 carbon atoms, where adjacent two or more among $R_1$ to $R_4$ may be connected with each other to form an aliphatic ring of 3 to 20 carbon atoms, an aromatic ring of 6 to 20 carbon atoms or a heteroaromatic ring of 4 to 20 carbon atoms; and $R_5$ to $R_{11}$ are each independently hydrogen; a silyl group; a halogen group; an alkyl group of 1 to 20 carbon atoms; an alkenyl group of 2 to 20 carbon atoms; a cycloalkyl group of 3 to 20 carbon atoms; an aryl group of 6 to 20 carbon atoms; an arylalkyl group of 7 to 20 carbon atoms; an alkylaryl group of 7 to 20 carbon atoms; an alkoxy group of 1 to 20 carbon atoms; or an aryloxy group of 6 to 20 carbon atoms; where adjacent two or more among $R_5$ to $R_{11}$ may be connected with each other to form an aliphatic ring of 3 to 20 carbon atoms, or an aromatic ring of 6 to 20 carbon atoms.

In an embodiment, X is O, S or a single bond,
M is a transition metal in group 4,
$Q_1$ and $Q_2$ are each independently hydrogen or an alkyl group of 1 to 12 carbon atoms,
$R_1$ to $R_4$ are each independently hydrogen; an alkyl group of 1 to 12 carbon atoms or an aryl group of 6 to 12 carbon atoms, where adjacent two or more among $R_1$ to $R_4$ may be connected with each other to form an aliphatic ring of 3 to 20 carbon atoms, an aromatic ring of 6 to 20 carbon atoms or a heteroaromatic ring of 4 to 20 carbon atoms, and
$R_5$ to $R_{11}$ are each independently hydrogen; an alkyl group of 1 to 12 carbon atoms or an aryl group of 6 to 12 carbon atoms.

In an embodiment, X is O, S or a single bond,
M is a transition metal in group 4,
$Q_1$ and $Q_2$ are each independently hydrogen or an alkyl group of 1 to 12 carbon atoms,
$R_1$ to $R_{11}$ are each independently hydrogen, an alkyl group of 1 to 12 carbon atoms or an aryl group of 6 to 12 carbon atoms.

In an embodiment, X is O, S or a single bond,
M is a transition metal in group 4,
$Q_1$ and $Q_2$ are each independently hydrogen or an alkyl group of 1 to 12 carbon atoms,
$R_3$ and $R_4$ are connected with each other to form a heteroaromatic ring of 4 to 20 carbon atoms,
$R_1$, $R_2$ and $R_5$ to $R_{11}$ are each independently hydrogen; an alkyl group of 1 to 12 carbon atoms or an aryl group of 6 to 12 carbon atoms.

If $R_3$ and $R_4$ are connected with each other to form a heteroaromatic ring of 4 to 20 carbon atoms, particularly, the transition metal compound according to the present invention may have a structure in which a transition metal in group 4 makes a coordination bond with a ligand compound including cyclopentadiene fused with benzothiophene, as in the following Formula 1-1:

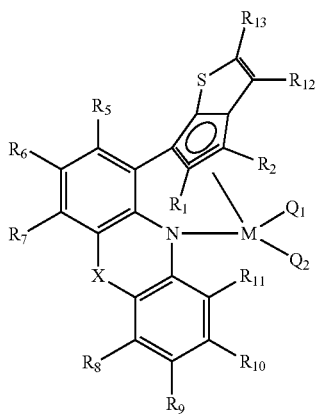

[Formula 1-1]

in Formula 1-1, X is O, S or a single bond,

M is a transition metal in group 4, $Q_1$ and $Q_2$ are each independently hydrogen or an alkyl group of 1 to 12 carbon atoms, and $R_1$, $R_2$ and $R_5$ to $R_{13}$ are each independently hydrogen, an alkyl group of 1 to 12 carbon atoms or an aryl group of 6 to 12 carbon atoms, where $R_{12}$ and $R_{13}$ may be connected with each other to form an aliphatic ring of 3 to 18 carbon atoms or an aromatic ring of 6 to 18 carbon atoms, and the aliphatic ring or the aromatic ring may be substituted with a halogen group, an alkyl group of 1 to 12 carbon atoms, an alkenyl group of 2 to 12 carbon atoms, or an aryl group of 6 to 12 carbon atoms.

In addition, in an embodiment, if the ligand compound of the present invention includes a carbazole group, in Formula 1, X is a single bond, M is a transition metal in group 4, $Q_1$ and $Q_2$ are each independently hydrogen or an alkyl group of 1 to 12 carbon atoms, $R_1$ to $R_4$ are each independently hydrogen, an alkyl group of 1 to 12 carbon atoms or an aryl group of 6 to 12 carbon atoms, where adjacent two or more among $R_1$ to $R_4$ may be connected with each other to form an aliphatic ring of 3 to 20 carbon atoms, an aromatic ring of 6 to 20 carbon atoms or a heteroaromatic ring of 4 to 20 carbon atoms, and $R_5$ to $R_{11}$ are each independently hydrogen, an alkyl group of 1 to 12 carbon atoms or an aryl group of 6 to 12 carbon atoms.

In an embodiment, if the ligand compound of the present invention includes phenothiazine or phenoxazine, in Formula 1, X is O or S, M is a transition metal in group 4, $Q_1$ and $Q_2$ are each independently hydrogen or an alkyl group of 1 to 12 carbon atoms, $R_1$ to $R_4$ are each independently hydrogen, an alkyl group of 1 to 12 carbon atoms or an aryl group of 6 to 12 carbon atoms, where adjacent two or more among $R_1$ to $R_4$ may be connected with each other to form an aliphatic ring of 3 to 20 carbon atoms, an aromatic ring of 6 to 20 carbon atoms or a heteroaromatic ring of 4 to 20 carbon atoms, and $R_5$ to $R_{11}$ are each independently hydrogen, an alkyl group of 1 to 12 carbon atoms or an aryl group of 6 to 12 carbon atoms.

Particularly, the transition metal compound of the present invention may be any one selected from the group consisting of the following structures:

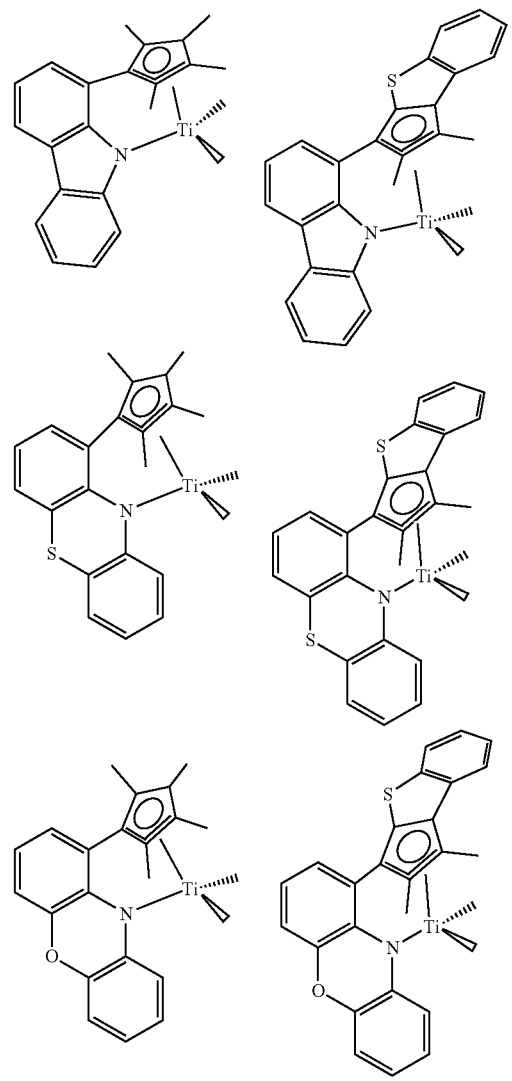

Another embodiment of the present invention provides a ligand compound represented by the following Formula 2:

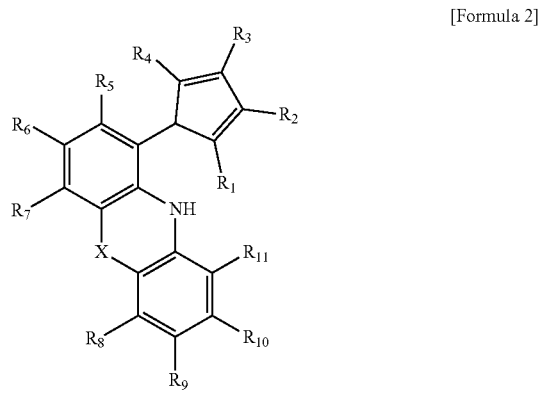

[Formula 2]

X is O, S or a single bond;

$R_1$ to $R_4$ are each independently hydrogen; a silyl group; an alkyl group of 1 to 20 carbon atoms; an alkenyl group of 2 to 20 carbon atoms; a cycloalkyl group of 3 to 20 carbon atoms; an aryl group of 6 to 20 carbon atoms; an alkylaryl group of 7 to 20 carbon atoms; an arylalkyl group of 7 to 20 carbon atoms; or a metalloid radical of a metal in group 14, which is substituted with a hydrocarbyl group of 1 to 20 carbon atoms; where adjacent two or more among $R_1$ to $R_4$ may be connected with each other to form an aliphatic ring of 3 to 20 carbon atoms, an aromatic ring of 6 to 20 carbon atoms or a heteroaromatic ring of 4 to 20 carbon atoms; and $R_5$ to $R_{11}$ are each independently hydrogen; a silyl group; a halogen group; an alkyl group of 1 to 20 carbon atoms; an alkenyl group of 2 to 20 carbon atoms; a cycloalkyl group of 3 to 20 carbon atoms; an aryl group of 6 to 20 carbon atoms; an arylalkyl group of 7 to 20 carbon atoms; an alkylaryl group of 7 to 20 carbon atoms; an alkoxy group of 1 to 20 carbon atoms; or an aryloxy group of 6 to 20 carbon atoms; where adjacent two or more among $R_5$ to $R_{11}$ may be connected with each other to form an aliphatic ring of 3 to 20 carbon atoms, or an aromatic ring of 6 to 20 carbon atoms.

If the ligand compound of the present invention includes a carbazole group, the ligand compound of the present invention may be prepared according to the following Reaction 1:

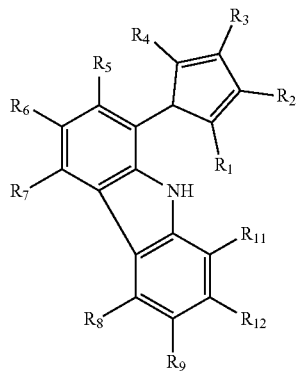

In addition, if the ligand compound of the present invention includes phenothiazine or phenoxazine, the ligand compound of the present invention may be prepared according to the following Reaction 2:

[Reaction 1]

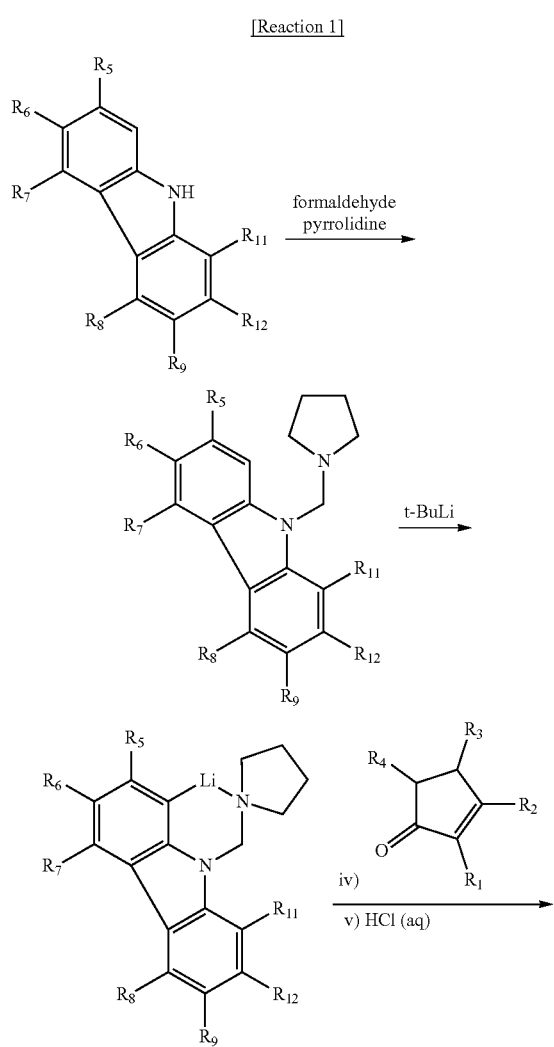

[Reaction 2]

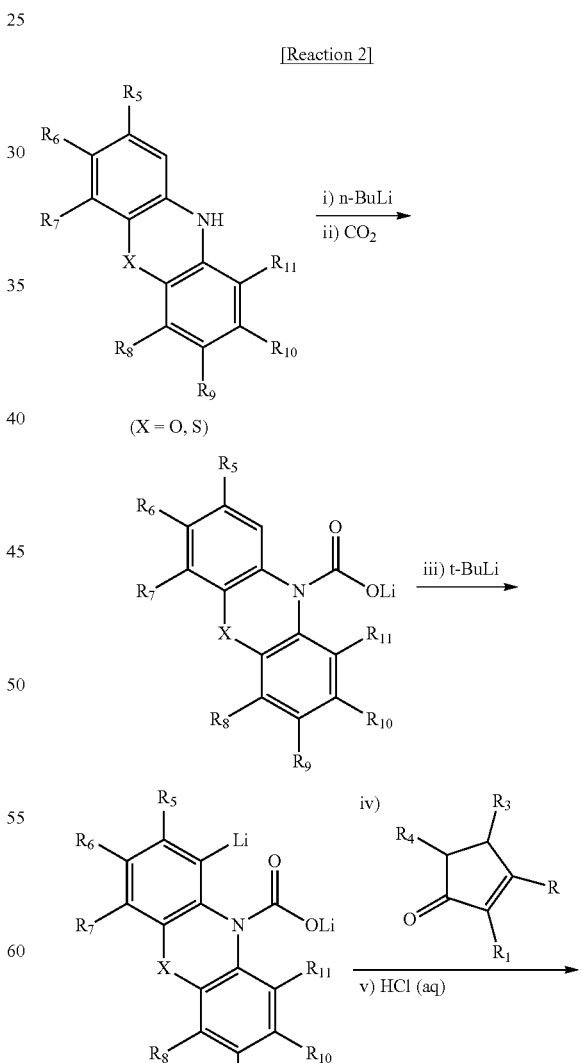

-continued

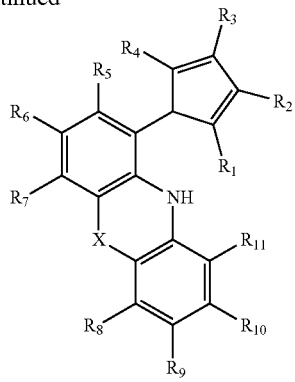

According to an embodiment of the present invention, the transition metal compound represented by Formula 1 may have a coordination bonded type of a transition metal in group 4 with the compound represented by Formula 2 as a ligand.

Particularly, by reacting a compound represented by Formula 2 with a compound represented by the following Formula 3, which is a precursor, and an organolithium compound, the transition metal compound of Formula 1, in which a transition metal in group 4 makes a coordination bond with the compound represented by Formula 2 as a ligand, may be obtained:

$$M(Q_1Q_2)_2 \quad \text{[Formula 3]}$$

In the above formulae, M, X, $Q_1$, and $Q_2$ are the same as defined in Formula 1.

Another embodiment of the present invention provides a catalyst composition for polymerizing polyolefin, including the transition metal compound.

The organolithium compound may be, for example, one or more selected from the group consisting of n-butyllithium, sec-butyllithium, methyllithium, ethyllithium, isopropyllithium, cyclohexyllithium, allyllithium, vinyllithium, phenyllithium and benzyllithium.

The compound represented by Formula 2 and the compound represented by Formula 3 may preferably be mixed in a molar ratio of 1:0.8 to 1:1.5, particularly, 1:1.0 to 1:1.1.

In addition, the organolithium compound may be used in an amount of 180 parts by weight to 250 parts by weight based on 100 parts by weight of the compound represented by Formula 2.

In the preparation method according to an embodiment of the present invention, the reaction may be performed in a temperature range of −80° C. to 140° C. for 1 to 48 hours.

The present invention also provides a catalyst composition including the compound of Formula 1.

The catalyst composition may further include a cocatalyst. The cocatalyst may be any one known in this art.

For example, the catalyst composition may further include at least one of the following Formulae 4 to 6 as a cocatalyst:

$$-[Al(R_{12})-O]_a- \quad \text{[Formula 4]}$$

In the above formula, each $R_{12}$ is independently a halogen group; a hydrocarbyl group of 1 to 20 carbon atoms; or a halogen-substituted hydrocarbyl group of 1 to 20 carbon atoms; and a is an integer of 2 or more;

$$D(R_{13})_3 \quad \text{[Formula 5]}$$

In the above formula, D is aluminum or boron; each $R_{13}$ is independently a halogen group; a hydrocarbyl group of 1 to 20 carbon atoms; or a halogen-substituted hydrocarbyl group of 1 to 20 carbon atoms; and $$[L-H]^+[Z(A)_4]^- \text{ or } [L]^+[Z(A)_4]^- \quad \text{[Formula 6]}$$

In the above formula, L is a neutral or a cationic Lewis acid; H is a hydrogen atom; Z is an element in group 13; and each A is independently an aryl group of 6 to 20 carbon atoms or an alkyl group of 1 to 20 carbon atoms, where one or more hydrogen atoms may be substituted with substituents; wherein the substituent is halogen, a hydrocarbyl group of 1 to 20 carbon atoms, an alkoxy group of 1 to 20 carbon atoms or an aryloxy group of 6 to 20 carbon atoms.

As a preparation method of the catalyst composition, there is provided a first preparation method including a step of obtaining a mixture by contacting the transition metal compound represented by Formula 1 with the compound represented by Formula 4 or Formula 5; and a step of adding the compound represented by Formula 6 to the mixture.

Also, there is provided a second preparation method of the catalyst composition including contacting the transition metal compound represented by Formula 1 with the compound represented by Formula 6.

In the first method of the preparation methods of the catalyst composition, the molar ratio of the compound represented by Formula 4 or Formula 5 with respect to the transition metal compound represented by Formula 1 may be from 1:2 to 1:5,000, particularly, from 1:10 to 1:1,000, more particularly, from 1:20 to 1:500.

If the molar ratio of the compound represented by Formula 4 or Formula 5 with respect to the transition metal compound represented by Formula 1 is less than 1:2, the amount of an alkylating agent is very small, and the alkylation of the metal compound may be incompletely achieved, and if the molar ratio is greater than 1:5,000, the alkylation of the metal compound may be performed, but side reactions between the remaining excessive amount of alkylating agent and the activating agent of Formula 6 may be performed, and the activation of the alkylated metal compound may be incompletely achieved.

In the second method of the preparation methods of the catalyst composition, the molar ratio of the compound represented by Formula 6 with respect to the transition metal compound of Formula 1 may be from 1:1 to 1:500, particularly, from 1:1 to 1:50, more particularly, from 1:2 to 1:25. If the molar ratio is less than 1:1, the amount of the activating agent is relatively small, the activation of the catalyst composition may be incompletely achieved, and the activity of the catalyst composition thus prepared may be reduced, and if the molar ratio is greater than 1:500, the activation of the metal compound may be completely achieved, but the excessive amount of activating agent remained may increase the unit cost of the catalyst composition, or the purity of the polymer thus prepared may decrease.

As the reaction solvent used during the preparation of the composition, a hydrocarbon solvent such as pentane, hexane, and heptane, or an aromatic solvent such as benzene, and toluene may be used, but the present invention is not limited thereto, and all solvents used in this technical field may be used.

In addition, the transition metal compound of Formula 1 and the cocatalyst may be used in a supported type by a support. Silica or alumina may be used as the support.

The compound represented by Formula 4 is not specifically limited as long as alkylaluminoxane is used. Particular examples thereof may include methylaluminoxane, ethylaluminoxane, isobutylaluminoxane, butylaluminoxane, etc., more particularly, methylaluminoxane.

The compound represented by Formula 5 is not specifically limited, and particular examples thereof may include trimethylaluminum, triethylaluminum, triisobutylaluminum, tripropylaluminum, tributylaluminum, dimethylchloroaluminum, triisopropylaluminum, tri-s-butylaluminum, tricyclopentylaluminum, tripentylaluminum, triisopentylaluminum, trihexylaluminum, trioctylaluminum, ethyldimethylaluminum, methyldiethylaluminum, triphenylaluminum, tri-p-tolylaluminum, dimethylaluminummethoxide, dimethylaluminumethoxide, trimethylboron, triethylboron, triisobutylboron, tripropylboron, tributylboron, etc., and more particularly, selected from trimethylaluminum, triethylaluminum, and triisobutylaluminum.

Examples of the compound represented by Formula 6 may include triethylammoniumtetraphenylboron, tributylammoniumtetraphenylboron, trimethylammoniumtetraphenylboron, tripropylammoniumtetraphenylboron, trimethylammoniumtetra(p-tolyl)boron, trimethylammoniumtetra(o,p-dimethylphenyl)boron, tributylammoniumtetra(p-trifluoromethylphenyl)boron, trimethylammoniumtetra(p-trifluoromethylphenyl)boron, tributylammoniumtetrapentafluorophenylboron, N,N-diethylaniliniumtetraphenylboron, N,N-diethylaniliniumtetraphenylboron, N,N-diethylaniliniumtetrapentafluorophenylboron, diethylammoniumtetrapentafluorophenylboron, triphenylphosphoniumtetraphenylboron, trimethylphosphoniumtetraphenylboron, triethylammoniumtetraphenylaluminum, tributylammoniumtetraphenylaluminum, trimethylammoniumtetraphenylaluminum, tripropylammoniumtetraphenylaluminum, trimethylammoniumtetra(p-tolyl)aluminum, tripropylammoniumtetra(p-tolyl)aluminum, triethylammoniumtetra(o,p-dimethylphenyl)aluminum, tributylammoniumtetra(p-trifluoromethylphenyl)aluminum, trimethylammoniumtetra(p-trifluoromethylphenyl)aluminum, tributylammoniumtetrapentafluorophenylaluminum, N,N-diethylaniliniumtetraphenylaluminum, N,N-diethylaniliniumtetraphenylaluminum, N,N-diethylaniliniumtetrapentafluorophenylaluminum, diethylammoniumtetrapentafluorophenylaluminum, triphenylphosphoniumtetraphenylaluminum, trimethylphosphoniumtetraphenylaluminum, triethylammoniumtetraphenylaluminum, tributylammoniumtetraphenylaluminum, trimethylammoniumtetraphenylboron, tripropylammoniumtetraphenylboron, trimethylammoniumtetra(p-tolyl)boron, tripropylammoniumtetra(p-tolyl)boron, triethylammoniumtetra(o,p-dimethylphenyl)boron, trimethylammoniumtetra(o,p-dimethylphenyl)boron, tributylammoniumtetra(p-trifluoromethylphenyl)boron, trimethylammoniumtetra(p-trifluoromethylphenyl)boron, tributylammoniumtetrapentafluorophenylboron, N,N-diethylaniliniumtetraphenylboron, N,N-diethylaniliniumtetraphenylboron, N,N-diethylaniliniumtetrapentafluorophenylboron, diethylammoniumtetrapentafluorophenylboron, triphenylphosphoniumtetraphenylboron, triphenylcarboniumtetra(p-trifluoromethylphenyl)boron, triphenylcarboniumtetrapentafluorophenylboron, etc.

A polyolefin homopolymer or copolymer may be prepared by contacting a catalyst composition including the transition metal compound of Formula 1; and one or more compounds selected from the compounds represented by Formula 4 to Formula 6, with one or more olefin monomers.

The most particular preparation process using the catalyst composition is a solution process. If the composition is used together with an inorganic support such as silica, it may also be applied to a slurry process or a gas phase process.

In the preparation process, the catalyst composition may be injected after being dissolved or diluted in an aliphatic hydrocarbon solvent of 5 to 12 carbon atoms such as pentane, hexane, heptane, nonane, decane, isomers thereof, an aromatic hydrocarbon solvent such as toluene and benzene, or a hydrocarbon solvent substituted with a chlorine atom such as dichloromethane and chlorobenzene, which are suitable for an olefin polymerization process. The solvent used may preferably be used after removing a small amount of water or air, which functions as a catalyst poison, by treating with a small amount of alkylaluminum, and may be used by further using a cocatalyst.

The olefin monomer which is polymerizable using the metal compound and the cocatalyst may include, for example, ethylene, alpha-olefin, cyclic olefin, etc., and a diene olefin-based monomer, a triene olefin-based monomer, etc. having two or more double bonds may also be polymerized. Particular examples of the monomer may include ethylene, propylene, 1-butene, 1-pentene, 4-methyl-1-pentene, 1-hexene, 1-heptene, 1-octene, 1-decene, 1-undecene, 1-dodecene, 1-tetradecene, 1-hexadecene, 1-icocene, norbornene, norbornadiene, ethylidenenorbornene, phenylnorbornene, vinylnorbornene, dicyclopentadiene, 1,4-butadiene, 1,5-pentadiene, 1,6-hexadiene, styrene, alpha-methylstyrene, divinylbenzene, 3-chloromethylstyrene, etc. Two or more of the monomers may be mixed and copolymerized.

Particularly, in the preparation method of the present invention, the catalyst composition has characteristics of preparing a copolymer having a high molecular weight, in a copolymerization reaction of ethylene and a monomer having large steric hindrance such as 1-octene even at a high reaction temperature of 90° C. or more.

In an embodiment, the polymer prepared by the preparation method of the present invention has a density of 0.855 to 0.915 g/cc, preferably, 0.855 to 0.870 g/cc.

In an embodiment, the polymer prepared by the preparation method of the present invention may have a melt index (190° C., 2.16 kg) measured based on ASTM D1238 of 0.01 to 100 g/10 minutes, preferably, 0.5 to 10 g/10 minutes.

Hereinafter, the present invention will be explained more particularly referring to the following examples. However, the examples are for assisting the understanding of the present invention, and the scope of the present invention is not limited thereto.

Synthesis of Ligand and Transition Metal Compounds

Organic reagents and solvents were purchased from Aldrich Co. and used after purifying by a standard method unless otherwise noted. In all steps of syntheses, air and humidity were blocked to increase the reproducibility of experiments. A compound in which tetramethyl cyclopentadiene is substituted in the ketone compounds of Formula 1 was synthesized according to document [*Organometallics* 2002, 21, 2842-2855].

Preparation of Ligand Compound

Example 1-1

[Formula 2-1]

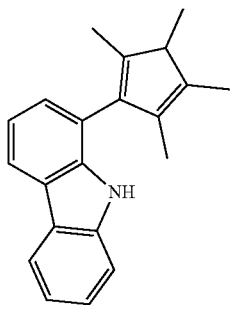

(1) Synthesis of 9-(Pyrrolidine-1-Yl Methyl)-9H-Carbazole (Compound (a))

To a well dried, Ar-substituted 250 ml schlenk flask, carbazole (10 g, 60 mmol), ethanol (120 ml), formaldehyde (37 wt % aq. Solution, 7.3 ml, 90 mmol) and pyrrolidine (7.5 ml, 90 mmol) were injected, followed by refluxing for 12 hours. After a certain time, the reaction solution cooled to room temperature was poured into a beaker containing 500 ml of distilled water. The resultant solution was extracted with ethyl acetate (200 ml) twice, and an organic layer was washed with water twice. The resultant solution was extracted with a 0.3 N HCl aqueous solution (100 ml) three times, and an aqueous layer was washed with ethyl acetate once. The aqueous layer was neutralized with 1 N KOH aqueous solution and then extracted with ethyl acetate. Organic layers were collected and then, dried with $Na_2CO_3$, filtered and concentrated to obtain 9-(pyrrolidine-1-yl methyl)-9H-carbazole (12.2 g, 81.5% yield). The product thus obtained was used in subsequent reaction without special separation.

$^1$H NMR (CDCl$_3$) δ 7.22-8.06 (m, 8H), 5.13 (s, 2H), 2.70 (m, 4H), 1.71 (m, 4H)

(b) Synthesis of [Formula 2-1]

To a well dried, Ar-substituted 250 ml schlenk flask, Compound (a) (5 g, 20 mmol) and anhydrous n-hexane (60 ml) were injected. After standing at −78° C., tert-butyl-lithium (1.7 M in n-pentane, 17.6 ml, 30 mmol) was slowly injected. The temperature of the reaction solution was slowly elevated to room temperature and stirring was performed overnight. Anhydrous tetrahydrofuran (20 ml) was injected and kept at −78° C. Then, 2,3,4,5-tetramethylcyclopent-2-en-1-one (4.52 ml, 30 mmol) was slowly injected thereto. The temperature of the reaction solution was slowly elevated to room temperature and stirring was performed overnight. After a certain time, a 3N HCl aqueous solution (200 ml) was injected, followed by stirring for 10 minutes. Then, the resultant product was extracted with ethyl acetate (200 ml) three times. Organic layers were collected, neutralized with trimethylamine, and washed with distilled water (100 ml) twice. Organic layers were collected, dried with $Na_2CO_3$, and filtered and solvents were evaporated. The crude product thus obtained was separated by column chromatography (n-hexane:ethyl acetate=20:1 (v/v)) to obtain [Formula 2-1] (3.1 g, 53.6% yield).

HRMS (EI): m/z calcd for ([M]$^+$ $C_{21}H_{21}N$) 287.4060, found 287.4060.

Example 2-1

[Formula 2-2]

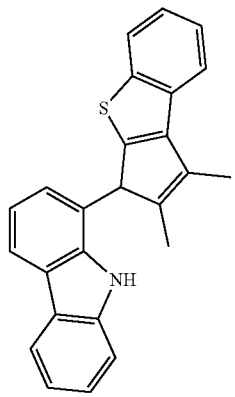

The same method as in Example 1 was performed except for injecting 1,2-dimethyl-1,2-dihydro-3H-benzo[b]cyclopenta[d]thiophene-3-one (6.5 g, 30 mmol) instead of 2,3,4,5-tetramethylcyclopent-2-en-1-one (4.52 ml, 30 mmol) to obtain [Formula 2-2] (3.6 g, 48.7% yield).

HRMS (EI): m/z calcd for ([M]$^+$ $C_{21}H_{21}N$) 365.4940, found 365.4943.

Example 3-1

[Formula 2-3]

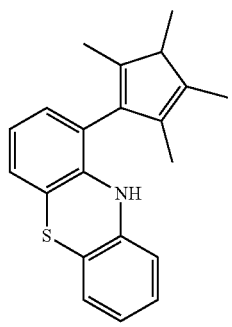

To a well dried, Ar-substituted 500 ml schlenk flask, phenothiazine (10 g, 50.2 mmol) of Aldrich Co., and anhydrous methyl tert-butyl ether (126 ml) were injected. After standing at −78° C., n-butyllithium (2.5 M in n-hexane, 22.1 ml, 55.2 mmol) was slowly injected. The temperature of the reaction solution was slowly elevated, followed by stirring for 4 hours. The reaction product was stood at −30° C. and anhydrous carbon dioxide was injected for 10 minutes by bubbling. After completing the injection, the temperature was slowly elevated to room temperature and stirring was performed overnight. Anhydrous tetrahydrofuran (12.6 ml) was injected and kept at −78° C. Then, tert-butyllithium (1.7 M in n-pentane, 50.2 ml, 85.3 mmol) was slowly injected thereto. The temperature of the reaction solution was slowly elevated to −20° C., and stirring was performed at −20° C.

for 2 hours. The reaction product was cooled to −78° C. again, and 2,3,4,5-tetramethylcyclopent-2-en-1-one (11.3 ml, 75.3 mmol) was slowly injected thereto. The temperature of the reaction solution was slowly elevated to room temperature and stirring was performed overnight. After a certain time, a 3N HCl aqueous solution (200 ml) was injected, followed by stirring for 10 minutes. Then, the resultant product was extracted with ethyl acetate (200 ml) three times. Organic layers were collected, neutralized with trimethylamine, and washed with distilled water (100 ml) twice. Organic layers were collected, dried with $Na_2CO_3$, and filtered and solvents were evaporated. The crude product thus obtained was separated by column chromatography (n-hexane:ethyl acetate=20:1 (v/v)) to obtain [Formula 2-3] (4.1 g, 25.5% yield).

HRMS (EI): m/z calcd for ([M]$^+$ $C_{21}H_{21}N$) 319.1395, found 319.1396.

Example 4-1

[Formula 2-4]

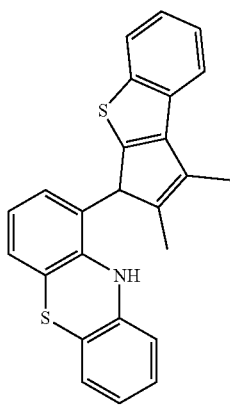

The same method as in Example 3 was performed except for injecting 1,2-dimethyl-1,2-dihydro-3H-benzo[b]cyclopenta[d]thiophene-3-one (16.3 g, 75.3 mmol) instead of 2,3,4,5-tetramethylcyclopent-2-en-1-one (11.3 ml, 75.3 mmol) to obtain [Formula 2-4] (5.6 g, 28.2% yield).

HRMS (EI): m/z calcd for ([M]$^+$ $C_{21}H_{21}N$) 397.0959, found 397.0961.

Preparation of Transition Metal Compound

Example 1-2

[Formula 1-1]

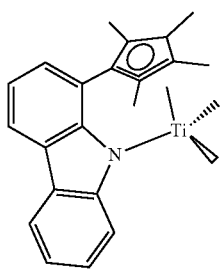

To a well dried, Ar-substituted 100 ml schlenk flask, [Formula 2-1] (1 g, 3.48 mmol) and anhydrous methyl tert-butyl ether (17.4 ml) were injected. After standing at −78° C., n-butyllithium (2.5 M in n-hexane, 2.9 ml, 7.31 mmol) was slowly injected. The temperature of the reaction solution was slowly elevated, followed by stirring for 4 hours. Then, methyllithium (1.6 M in diethyl ether, 4.6 ml, 7.31 mmol) was injected, and then, stood at −20° C. Then, titanium (IV) chloride (1.0 M in toluene, 3.5 ml, 3.5 mmol) was injected thereto. After finishing the injection, the temperature was slowly elevated to room temperature, and stirring was performed at room temperature overnight. The resultant product was vacuum dried and extracted by injecting anhydrous n-hexane (50 ml), and then, filtered via glass frit with a celite pad. The filtrate was vacuum dried to obtain [Formula 1-1] (0.96 g, 75.9% yield).

$^1$H NMR ($C_6D_6$): δ 8.44 (d, 1H), 8.20 (d, 1H), 7.60 (m, 2H), 7.46 (t, 1H), 7.25 (m, 2H), 2.10 (s, 6H), 1.72 (s, 6H), 0.66 (s, 6H)

Example 2-2

[Formula 1-2]

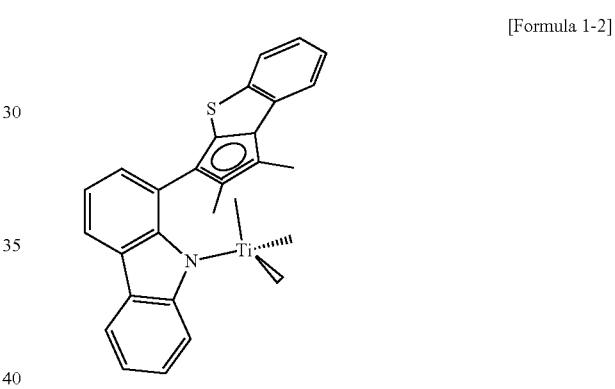

To a well dried, Ar-substituted 100 ml schlenk flask, [Formula 2-2] (1 g, 2.74 mmol) and anhydrous methyl tert-butyl ether (13.7 ml) were injected. After standing at −78° C., n-butyllithium (2.5 M in n-hexane, 2.3 ml, 5.75 mmol) was slowly injected. The temperature of the reaction solution was slowly elevated to room temperature, followed by stirring for 4 hours. Then, methyllithium (1.6 M in diethyl ether, 3.6 ml, 5.75 mmol) was injected, and then, stood at −20° C. Then, titanium (IV) chloride (1.0 M in toluene, 2.7 ml, 2.7 mmol) was injected thereto. After finishing the injection, the temperature was slowly elevated to room temperature, and stirring was performed at room temperature overnight. The resultant product was vacuum dried and extracted by injecting anhydrous n-hexane (50 ml), and then, filtered via glass frit with a celite pad. The filtrate was vacuum dried to obtain [Formula 1-2] (0.84 g, 69.4% yield).

$^1$H NMR ($C_6D_6$): δ 8.42 (d, 1H), 8.19 (d, 1H), 7.99 (d, 1H), 7.68 (d, 1H), 7.60 (m, 2H), 7.45 (t, 1H), 7.40 (dd, 1H), 7.30 (dd, 1H), 7.22 (m, 2H), 2.72 (s, 3H), 2.08 (s, 3H), 0.62 (s, 3H), 0.60 (s, 3H)

Example 3-2

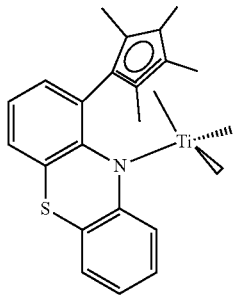
[Formula 1-3]

To a well dried, Ar-substituted 100 ml schlenk flask, [Formula 2-3] (1 g, 3.13 mmol) and anhydrous methyl tert-butyl ether (15.7 ml) were injected. After standing at −78° C., n-butyllithium (2.5 M in n-hexane, 2.6 ml, 6.57 mmol) was slowly injected. The temperature of the reaction solution was slowly elevated to room temperature, followed by stirring for 4 hours. Then, methyllithium (1.6 M in diethyl ether, 4.1 ml, 6.57 mmol) was injected, and then, stood at −20° C. Then, titanium (IV) chloride (1.0 M in toluene, 3.1 ml, 3.1 mmol) was injected thereto. After finishing the injection, the temperature was slowly elevated to room temperature, and stirring was performed at room temperature overnight. The resultant product was vacuum dried and extracted by injecting anhydrous n-hexane (50 ml), and then, filtered via glass frit with a celite pad. The filtrate was vacuum dried to obtain [Formula 1-3] (0.88 g, 71.4% yield).

$^1$H NMR ($C_6D_6$): δ 7.67 (dd, 1H), 7.36-7.41 (m, 4H), 7.17 (m, 2H), 2.09 (s, 6H), 1.75 (s, 6H), 0.60 (s, 6H)

Example 4-2

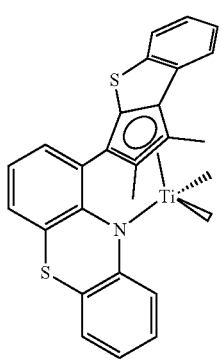
[Formula 1-4]

The same method as in Example 3-1 was performed except for using [Formula 2-4] instead of [Formula 2-3] to obtain [Formula 1-4] (1.00 g, 84.0% yield).

$^1$H NMR ($C_6D_6$): δ 8.25 (1H, d), 8.13 (1H, d), 7.67-7.69 (3H, m), 7.36-7.41 (4H, m), 7.17 (m, 2H), 2.02 (s, 3H), 1.81 (s, 3H), 0.61 (s, 3H), 0.58 (s, 3H)

Comparative Example 1

A compound represented by Formula 1-5 below was prepared by the method described in document "Organometallics, 2007, 26, 6685-6687".

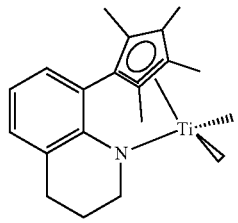
[Formula 1-5]

Synthesis of Ethylene/1-Octene Copolymer

Example 5

To a 2 L autoclave reactor under about 50° C., anhydrous n-hexane (1 L), 1-octene (200 ml) and a triisobutylaluminum solution (1.0 M in n-hexane, 0.3 ml) were added, and the reactor was ventilated so that the internal pressure of the reactor was 10 psi. The reactor was pre-heated to 150° C. and ethylene was injected by 500 psi. A dimethylanilinium tetrakis(pentafluorophenyl) borate cocatalyst solution (5.0 mM in toluene, 4 ml) was injected into a catalyst storing tank, and then injected into the reactor by applying argon with high pressure, and a transition metal compound catalyst solution of Example 1-2 (2.0 mM in n-hexane, 1 ml), treated with a triisobutylaluminum compound, was injected into the reactor. Then, a polymerization reaction was initiated by applying argon with a high pressure of about 30 bar. The polymerization reaction was performed for 8 minutes. The reaction heat was removed through a cooling coil in the reactor to maximally keep the polymerization temperature constant. After performing the polymerization reaction for 8 minutes, the remaining gas was exhausted out, and a polymer solution was discharged via a bottom part. An excessive amount of ethanol was added thereto to cool the polymer solution and induce precipitation. The polymer thus obtained was washed with ethanol and acetone twice or three times, respectively, and dried in a vacuum oven at 90° C. for 12 hours or more, and the physical properties thereof were measured.

Example 6

The same method as in Example 5 was performed except for using the transition metal compound prepared in Example 2-2 instead of the transition metal compound prepared in Example 1-2, to prepare an ethylene/1-octene copolymer.

Example 7

The same method as in Example 5 was performed except for using the transition metal compound prepared in Example 3-2 instead of the transition metal compound prepared in Example 1-2, to prepare an ethylene/1-octene copolymer.

Example 8

The same method as in Example 5 was performed except for using the transition metal compound prepared in Example 4-2 instead of the transition metal compound prepared in Example 1-2, to prepare an ethylene/1-octene copolymer.

Comparative Example 2

The same method as in Example 5 was performed except for using the transition metal compound prepared in Comparative Example 1 instead of the transition metal compound prepared in Example 1-2, to prepare an ethylene/1-octene copolymer.

Experimental Examples: Measurement of Physical Properties of 1-Octene Copolymer With respect to the ethylene/1-octene copolymers prepared in Examples 5 to 8 and Comparative Example 2, density, melting index and melting temperature were measured.

1) Density of polymer: A sheet with a thickness of 3 mm and a radius of 2 mm was manufactured using a press mold at 190° C. and cooled in a rate of 10° C./min, and then, measurement was performed using a Mettler balance.

2) Melt index (MI) of polymer: Measurement was performed according to ASTM D-1238 (190° C., 2.16 kg load).

3) Melting temperature (Tm) of polymer: Measurement was performed using Q100 of TA Co., and measurement values were obtained through second melting after elevating in a rate of 10° C. per minute to synchronize the thermal hysteresis of a polymer.

Physical properties were measured for Examples 5 to 8 and Comparative Example 2 according to the methods above, and the results are listed in Table 1 below.

TABLE 1

| | Catalyst (transition metal compound) | Density (unit: g/cc) | Melt index (unit: g/10 min) | Melting temperature (unit: ° C.) |
|---|---|---|---|---|
| Example 5 | Formula 1-1 | 0.863 | 5.3 | 52 |
| Example 6 | Formula 1-2 | 0.867 | 2.6 | 57 |
| Example 7 | Formula 1-3 | 0.870 | 1.2 | 61 |
| Example 8 | Formula 1-4 | 0.862 | 0.9 | 52 |
| Comparative Example 2 | Formula 1-5 | 0.875 | 2.9 | 64 |

As shown in Table 1, if the transition metal compound according to the present invention is used as a polymerization reaction catalyst for the preparation of an olefin-based polymer, an olefin-based copolymer having a high molecular weight in a low density region may be prepared when compared with the transition metal compound according to the Comparative Example.

Particularly, a copolymer prepared using a catalyst including the transition metal compound of an embodiment of the present invention showed lower density than a case using the catalyst of the Comparative Example. If the density of the copolymer decreases, melting temperature also decreases, and from the melting temperature results in Table 1, it is supported that the copolymers according to the embodiments of the present invention are in a low-density region.

In addition, in the production of an olefin copolymer, if the ratio of higher alpha olefin (HAO) in a copolymer increases, i.e., if high copolymerization properties are achieved, the density of a copolymer decreases. Accordingly, from the results, it may be found that the HAO ratio in the copolymer prepared using the catalyst including the transition metal compound of an embodiment of the present invention is high, i.e., high copolymerization properties are achieved.

In addition, the copolymer prepared using the catalyst including the transition metal compound of an embodiment of the present invention showed low melting index (MI) overall, and particularly, the copolymers according to Examples 6 to 8 showed low melting index when compared with the catalyst of the Comparative Example. There is correlation between melting index and molecular weight of a copolymer, and if the melting index decreases, the molecular weight may increase. Accordingly, from the results on the melting index in Table 1, it may be confirmed that the copolymer prepared according to an embodiment of the present invention has a high molecular weight.

The invention claimed is:

1. A ligand compound represented by Formula 2:

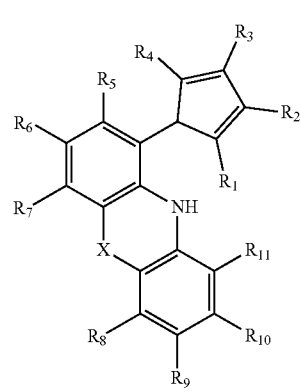

[Formula 2]

X is O, S or a single bond;

$R_1$ to $R_4$ are each independently hydrogen; a silyl group; an alkyl group of 1 to 20 carbon atoms; an alkenyl group of 2 to 20 carbon atoms; a cycloalkyl group of 3 to 20 carbon atoms; an aryl group of 6 to 20 carbon atoms; an alkylaryl group of 7 to 20 carbon atoms; or an arylalkyl group of 7 to 20 carbon atoms, where adjacent two or more among $R_1$ to $R_4$ are optionally connected with each other to form an aliphatic ring of 3 to 20 carbon atoms, an aromatic ring of 6 to 20 carbon atoms or a heteroaromatic ring of 4 to 20 carbon atoms; and $R_5$ to $R_{11}$ are each independently hydrogen; a silyl group; a halogen group; an alkyl group of 1 to 20 carbon atoms; an alkenyl group of 2 to 20 carbon atoms; a cycloalkyl group of 3 to 20 carbon atoms; an aryl group of 6 to 20 carbon atoms; an arylalkyl group of 7 to 20 carbon atoms; an alkylaryl group of 7 to 20 carbon atoms; an alkoxy group of 1 to 20 carbon atoms; or an aryloxy group of 6 to 20 carbon atoms; where adjacent two or more among $R_5$ to $R_{11}$ are optionally connected with each other to form an aliphatic ring of 3 to 20 carbon atoms, or an aromatic ring of 6 to 20 carbon atoms.

2. A method of preparing a transition metal compound of Formula 1, comprising reacting the ligand compound according to claim 1 with titanium (IV) chloride and methyllithiuman:

[Formula 1]
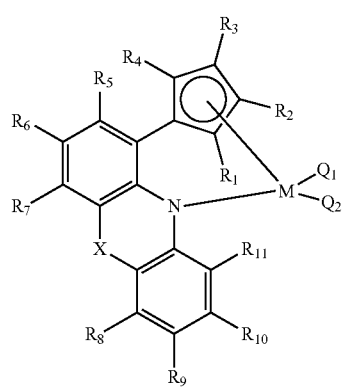
X, and $R_1$ to $R_{11}$ are the same as defined in claim 1,
M is Ti; and
$Q_1$ and $Q_2$ are each methyl.
* * * * *